US008624042B2

(12) United States Patent
Grasset et al.

(10) Patent No.: US 8,624,042 B2
(45) Date of Patent: Jan. 7, 2014

(54) PROCESS FOR DIMERIZATION OF ETHYLENE TO BUT-1-ENE USING A COMPOSITION COMPRISING A TITANIUM-BASED COMPLEX AND AN ALKOXY LIGAND FUNCTIONALIZED BY A HETEROATOM

(75) Inventors: Fabien Grasset, Bron (FR); Lionel Magna, Lyons (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 0 days.

(21) Appl. No.: 13/109,377

(22) Filed: May 17, 2011

(65) Prior Publication Data
US 2011/0288308 A1    Nov. 24, 2011

(30) Foreign Application Priority Data

May 18, 2010  (FR) ..................................... 10 02089

(51) Int. Cl.
C07F 7/28    (2006.01)
C07F 9/50    (2006.01)
C07C 2/76    (2006.01)
B01J 31/14   (2006.01)

(52) U.S. Cl.
USPC ............... 549/210; 502/103; 556/21; 556/54; 585/601

(58) Field of Classification Search
None
See application file for complete search history.

(56) References Cited

U.S. PATENT DOCUMENTS

| 3,879,485 A | 4/1975 | Belov et al. |
| 4,101,600 A | 7/1978 | Zhukov et al. |
| 2007/0135600 A1 | 6/2007 | Otomaru et al. |
| 2011/0213190 A1 | 9/2011 | Cazaux |

FOREIGN PATENT DOCUMENTS

| CA | 1 298 829 C | 4/1992 | |
| FR | 2 341 540 A1 | 9/1977 | |
| FR | 2 916 199 A1 | 11/2008 | |
| FR | 2916199 | * 11/2008 | .............. C07C 11/08 |

OTHER PUBLICATIONS

Szczegot et al. Polimery (Warsaw, Poland), 22(11), pp. 399-401.*
Ivolgina et al. Neftekhimiya, vol. 27, Issue 3, pp. 369-371, 1987, and an English translated Abstract cited from SciFinder.*
Cazaux, JB, et al., "Mono(aryloxido)Titanium(IV) Complexes and Their Application in the Selective Dimerization of Ethylene," European Journal of Inorganic Chemistry, 2009, pp. 2942-2950; Cited in Search Report, dated Dec. 15, 2010, issued in corresp FR10/02.089.
Search Report, dated Dec. 15, 2010, issued in corresponding FR10/02.089.
Szczegot, K. et al. "Catalytic activity of organometallic Al-Ti complexes containing aminoalkoxlyl ligands in the process of ethylene polymerization," Research Work, Institute of Chemistry, Pedagogical University, Opole, Poland. 22(11), 399-401 (1977).

* cited by examiner

*Primary Examiner* — Yun Qian
(74) *Attorney, Agent, or Firm* — Millen, White, Zelano & Branigan, P.C.

(57) ABSTRACT

The invention describes a process for the selective dimerization of ethylene to but-1-ene using a catalytic composition comprising at least one organometallic titanium complex, said organometallic complex containing at least one alkoxy type ligand functionalized by a heteroatom selected from nitrogen, oxygen, phosphorus, sulphur, arsenic and antimony or by an aromatic group.

20 Claims, No Drawings

PROCESS FOR DIMERIZATION OF ETHYLENE TO BUT-1-ENE USING A COMPOSITION COMPRISING A TITANIUM-BASED COMPLEX AND AN ALKOXY LIGAND FUNCTIONALIZED BY A HETEROATOM

The present invention relates to the selective dimerization of ethylene to but-1-ene. One aim of the invention is to provide a process for the dimerization of ethylene using a particular catalytic composition.

PRIOR ART

It is well known that olefins such as ethylene, propylene or but-1-ene can be dimerized with catalytic systems based on transition metals such as nickel, chromium, titanium, zirconium or other metals, in the presence of a co-catalyst such as a hydrocarbylaluminium compound, a hydrocarbylaluminium halide or an aluminoxane.

Several types of ligands have been described for stabilizing the catalytic species and for orientating the selectivity of the dimerization reaction. In U.S. Pat. No. 2,943,125, K Ziegler describes a method for the dimerization of ethylene to but-1-ene using a catalyst obtained by mixing trialkylaluminium and a titanium or zirconium tetra-alcoholate. During the reaction, a certain quantity of high molecular mass polyethylene is also formed, which considerably complicates the procedure. A number of improvements have been proposed for reducing the quantity of polymer, in particular in U.S. Pat. No. 3,686,350, which recommends the use of organic phosphorus compounds jointly with the elements of the catalyst, in U.S. Pat. No. 4,101,600, which describes the treatment of the catalyst with hydrogen or in U.S. Pat. No. 3,879,485, which describes the use of various ethers as solvents for the reaction medium. Although those modifications to the initial catalytic system substantially improve the selectivity of the reaction, they turn out to be of little practical use, in particular in an industrial process in which the but-1-ene has to be separated from the solvent, leaving only traces of the polar compound in the butene. From this point of view, patent FR 2 552 079 demonstrated that the use of an ether in association with an alkyl titanate in a near-stoichiometric quantity and of a trihydrocarbylaluminium appreciably improved the activity and selectivity of alkyl titanate-trihydrocarbylaluminium catalysts for the dimerization of ethylene to but-1-ene. This effect is more marked that that brought about by the use of ethers in a quantity corresponding to a use as a solvent. It also has the advantage of eliminating the use of said ethers as solvents, the disadvantages of which have been indicated.

The principal disadvantage of catalytic systems based on titanium resulting in the selective formation of but-1-ene is the formation of a non-negligible quantity of polymers. This polymer formation may be at the origin of a rapid deactivation of the catalyst as well as a considerable difficulty in operability in an industrial unit. Control of the quantity of polymers is thus a very important parameter for the industrial future of this type of catalytic system.

Control of the co-production of polymers constitutes a major part of systems associated with the use of additives (organic or otherwise) which very often form complexes with the catalytic composition. Further, although they perform well in controlling the production of polyethylene (PE), those additives often result in reductions in productivity of the catalyst.

One aim of the invention is to provide a novel catalytic composition for the selective dimerization of ethylene to but-1-ene.

Another aim of the invention is to provide a process for the selective dimerization of ethylene to but-1-ene employing said catalytic composition, said process having an improved catalytic activity.

DESCRIPTION OF THE INVENTION

It has now been discovered that a process employing a catalytic composition comprising at least one organometallic titanium complex, said organometallic complex containing at least one alkoxy type ligand functionalized by a heteroatom selected from nitrogen, oxygen, phosphorus, sulphur, arsenic and antimony or by an aromatic group and having the general formula:

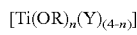

in which:
Y is a hydrocarbyl radical containing 1 to 30 carbon atoms or a radical selected from the group formed by halides, R'O— alkoxy groups, R'$_2$N— amido groups and R'COO— carboxylates, where R' is a hydrocarbyl radical, preferably non-functionalized, containing 1 to 30 carbon atoms;
n can take whole values from 1 to 4;
the ligand —OR is an organic compound selected from the family of alkoxy ligands the general structure of which is proposed below:

in which:
the functional group L is a group comprising a heteroatom selected from nitrogen, oxygen, phosphorus, sulphur, arsenic and antimony or an aromatic group;
the group X represents a hydrocarbon group ($CR^7R^8$), an oxygen atom or a group comprising a nitrogen atom, —$NR^9$;
the groups $R^7$, $R^8$, $R^9$, $R^{10}$ and $R^{11}$ represent a hydrogen atom or a hydrocarbon chain, which may or may not be cyclic, containing 1 to 30 carbon atoms, and optionally comprising a heteroatom;
n may take whole values from 0 to 30, preferably 0 to 10;
can be used to obtain a very high selectivity for the selective dimerization of ethylene to but-1-ene and to limit the formation of polymers.

In the context of the invention, the term "alkoxy" is defined as a group having general formula —OR in which the group R is an alkyl or substituted alkyl group. This definition of the term "alkoxy" does not include groups of the aryloxy or phenoxy type. In the catalytic composition of the invention, the alkoxy type ligand as defined hereinabove is functionalized by a heteroatom selected from nitrogen, oxygen, phosphorus, sulphur, arsenic and antimony or by an aromatic group and has the claimed formulation.

Preferably, said functional group L is a group comprising a heteroatom, said group comprising a heteroatom being selected from the groups —$NR^1R^2$, —$OR^3$, —$PR^4R^5$ and —$SR^6$, in which the groups $R^1$, $R^2$, $R^3$, $R^4$, $R^5$, $R^6$ represent a hydrogen atom or a hydrocarbon chain, which may or may not be cyclic, containing 1 to 30 carbon atoms.

Preferably, Y is a radical selected from the group formed by R'O— alkoxy where R' is a hydrocarbyl radical, preferably non-functionalized, containing 1 to 30 carbon atoms. Preferably again, Y is a chlorine atom.

Preferably, the group ($CR^{10}R^{11}$)$_n$ is selected from the following groups: —$CH_2$—, —$(CH_2)_2$—, —$(CH_2)_3$—, —(CH$_2$)$_4$—, —(CH$_2$)$_5$—, —C(CH$_3$)$_2$—, —C(CH$_3$)$_2$—CH$_2$—, —C(CH$_3$)$_2$—CH$_2$—CH$_2$—, —C(CF$_3$)$_2$—, —C(CF$_3$)$_2$—CH$_2$— and —C(CF$_3$)$_2$—CH$_2$—CH$_2$—.

Preferably, said functional group L is selected from the following groups: methoxy (—OMe), butoxy (—OBu), dimethylamino (—NMe$_2$), pyrrolidino (C$_4$H$_8$N), pyridino (—C$_5$H$_4$N), phosphino (—PR$_2$), in which R is an alkyl or aryl group which may or may not be substituted, thiophene (—C$_4$H$_3$S), tetrahydrofuran (—C$_4$H$_7$O), furan (—C$_4$H$_3$O) and phenyl (—C$_6$H$_5$), said groups possibly being substituted or non-substituted. Said group L is preferably the phosphino group (—PR$_2$) in which R is an alkyl or aryl group which may or may not be substituted.

Preferably, X represents a hydrocarbon group (CR$^7$R$^8$). Highly preferably, X is a hydrocarbon group (CR$^7$R$^8$) selected from the groups —CH$_2$— and —C(CH$_3$)$_2$—.

The catalytic composition used in the process for the selective dimerization of ethylene to but-1-ene of the invention may advantageously also contain a hydrocarbylaluminium compound, termed the activating agent, selected from the group formed by tris(hydrocarbyl)aluminium compounds, chlorinated or brominated hydrocarbylaluminium compounds and aluminoxanes.

The tris(hydrocarbyl)aluminium compounds and chlorinated and brominated hydrocarbylaluminium compounds preferably have the general formula AlR"$_x$Z$_{3-x}$, in which R" represents a monovalent hydrocarbon radical containing up to 12 carbon atoms, for example, such as alkyl, aryl, aralkyl, alkaryl or cycloalkyl, Z represents a halogen atom selected, for example, from chlorine and bromine, Z preferably being a chlorine atom; x takes a value from 1 to 3. Examples of such compounds with formula AlR"$_x$Z$_{3-x}$ which may be mentioned are ethylaluminium sesquichloride (Et$_3$Al$_2$Cl$_3$), dichloroethylaluminium (EtAlCl$_2$), dichoroisobutylaluminium (iBuAlCl$_2$), chlorodiethylaluminium (Et$_2$AlCl) and triethylaluminium (AlEt$_3$). Examples of aluminoxanes which may be used in the invention which may be cited are methylaluminoxane and modified methylaluminoxane (MMAO). These activating agents may be used alone or as a mixture.

Depending on the nature of the organometallic complex [Ti(OR)$_n$(Y)$_{(4-n)}$], the activating agent may also be selected from the group of Lewis acids of the tris(aryl)borane type such as tris(perfluorophenyl)borane, tris(3,5-bis(trifluoromethyl)phenyl)borane, tris(2,3,4,6-tetrafluorophenyl)borane, tris(perfluoronaphthyl)borane, tris(perfluorobiphenyl)borane and derivatives thereof. It is also possible to use as the activating agent an (aryl)borate associated with a triphenylcarbenium cation or a tri-substituted ammonium cation such as triphenylcarbenium tetrakis(perfluorophenyl)borate, N,N-dimethylanilinium tetrakis(perfluorophenyl)borate, N,N-diethylanilinium tetrakis(3,5-bis(trifluoromethyl)phenyl)borate, or triphenylcarbenium tetrakis(3,5-bis(trifluoromethyl)phenyl)borate.

Without wishing to be bound by any particular theory, the functional group L which is characterized by the presence of a heteroatom selected from nitrogen, oxygen, phosphorus, sulphur, antimony and arsenic or by the presence of an aromatic group is capable of interacting with the metallic centre Ti, thus forming a bond, for example of the dative type, thereby favouring the formation of a complex which is active in catalysis and contributing to its stability. Without being limiting, the examples below illustrate the "O—(CR$^{10}$R$^{11}$)$_n$—X-L" ligands of the invention. The ligands are represented below in their protonated form:

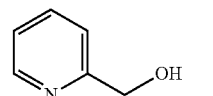
L1

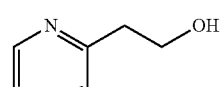
L2

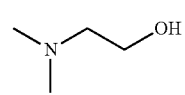
L3

L4

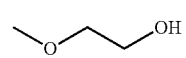
L5

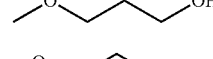
L6

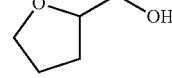
L7

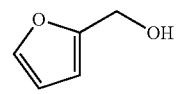
L8

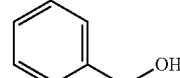
L9

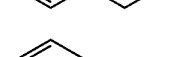
L10

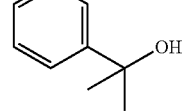
L11

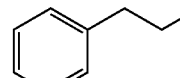
L12

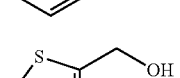
L13

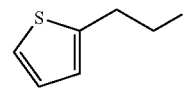
L14

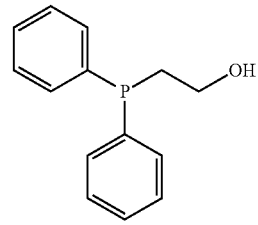

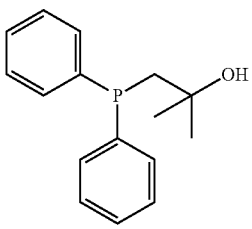

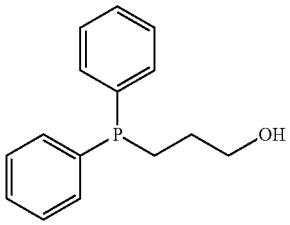

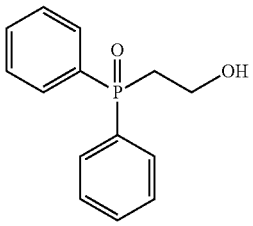

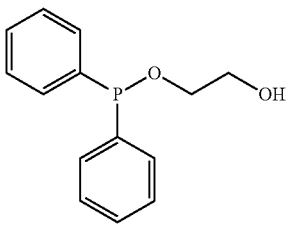

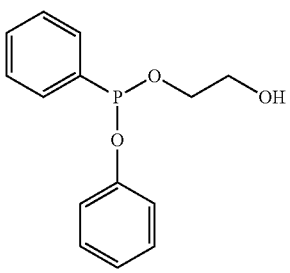

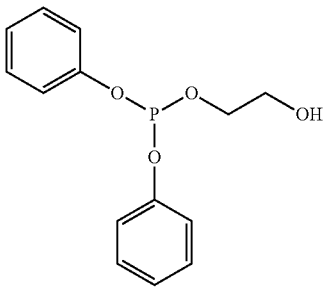

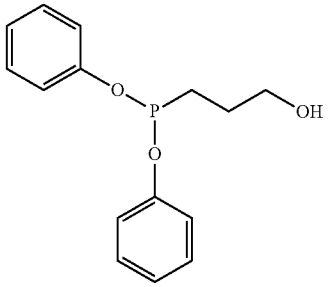

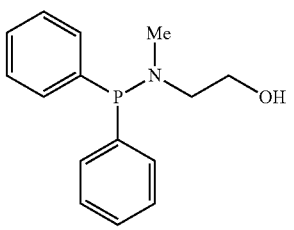

Process for Preparing an Organometallic Complex

The process for preparing an organometallic titanium complex for the catalytic composition used in the process of the invention is carried out using methods which are known in the literature concerning the synthesis of organometallic complexes comprising at least one alkoxy ligand. Any process for the preparation of this compound may be suitable, such as the reaction of an alkoxy type ligand functionalized by a heteroatom selected from nitrogen, oxygen, phosphorus or sulphur or by an aromatic group with a titanium salt, directly or in the presence of an organic solvent such as an ether, for example, an alkane such as pentane or cyclohexane, for example, an aromatic solvent such as toluene, for example, or a chlorinated solvent such as dichloromethane or chlorobenzene, for example.

In accordance with a preferred implementation of said preparation process, the organometallic complex is prepared in situ in the solvent used for the dimerization reaction. In this case, the order in which the titanium salt is mixed is not critical. However, preferably, a solution of a soluble titanium compound is initially prepared in an organic medium and then the alkoxy type ligand functionalized by a heteroatom selected from nitrogen, oxygen, phosphorus or sulphur or by an aromatic group is added.

In accordance with a preferred implementation of said preparation process, said organometallic complex is isolated before dissolving in the solvent for the dimerization reaction.

Process for Preparing a Catalytic Composition Used in the Process of the Invention In accordance with a preferred implementation of the process for preparing said catalytic composition and when an activating agent is used, the two components of said catalytic composition, i.e. the organometallic complex [Ti(OR)$_n$(Y)$_{(4-n)}$] and the activating agent, may be brought into contact in any order in a solvent selected from the group formed by aliphatic and cycloaliphatic hydrocarbons such as hexane, cyclohexane, heptane, butane or isobutane, by an unsaturated hydrocarbon such as a mono-olefin or a diolefin containing 4 to 20 carbon atoms, for example, by an aromatic hydrocarbon such as benzene, toluene, ortho-xylene, mesitylene or ethylbenzene, or by a chlorinated hydrocarbon such as chlorobenzene or dichloromethane, pure or as a mixture. Advantageously, aliphatic hydrocarbons such as cyclohexane or n-heptane and aromatic hydrocarbons such as ortho-xylene are used.

In accordance with another preferred implementation of the process for preparing said catalytic composition and when an activating agent is used, the activating agent is added to a solution containing the organometallic titanium complex.

The concentration of titanium in the catalytic solution is advantageously in the range $1 \times 10^{-4}$ to 1 mole/L, preferably in the range $1 \times 10^{-3}$ to 0.5 mole/L.

The molar ratio between the optional activating agent and the organometallic titanium complex is advantageously in the range 1/1 to 2000/1, preferably in the range 2/1 to 800/1 and more preferably in the range 2/1 to 500/1.

The temperature at which the components of the catalytic system are mixed is advantageously in the range $-10°$ C. to $180°$ C., preferably in the range $0°$ C. to $+150°$ C., for example at a temperature close to ambient temperature ($15°$ C. to $30°$ C.). The mixture may be produced in an atmosphere of ethylene or an inert gas.

Dimerization Reaction

The process of the invention is a process for the selective dimerization of ethylene to but-1-ene employing the catalytic composition described above.

In a preferred implementation, titanium metal is used, along with triethylaluminium as the activating agent and a molar ratio of activating agent to titanium in the range 1 to 5 for the dimerization of ethylene.

The ethylene dimerization reaction is advantageously carried out at a total pressure of 0.5 to 15 MPa, preferably in the range 1 to 10 MPa, and at a temperature of $20°$ C. to $180°$ C., preferably $40°$ C. to $140°$ C.

In accordance with a preferred embodiment, the dimerization reaction is carried out batchwise. A selected volume of catalytic solution constituted as described above is introduced into a reactor provided with the usual stirring, heating and cooling devices, then pressurized with ethylene to the desired pressure, and the temperature is adjusted to the desired value. The dimerization reactor is kept at a constant pressure by introducing ethylene until the total volume of liquid produced represents, for example, 2 to 50 times the volume of the catalytic solution originally introduced. Next, the catalyst is destroyed using any normal means known to the skilled person, then the reaction products and the solvent are extracted and separated.

In accordance with another preferred implement, the catalytic dimerization reaction is carried out continuously. The catalytic solution is injected at the same time as the ethylene into a reactor stirred by conventional mechanical means known to the skilled person or by external re-circulation, and held at the desired temperature. It is also possible to separately inject the components of the catalyst into the reaction medium. The ethylene is introduced via a pressure-operated inlet valve which keeps it constant. The reaction mixture is extracted using a liquid level-actuated valve which keeps that level constant. The catalyst is continuously destroyed using any normal means known to the skilled person, then the products from the reaction as well as the solvent are separated, for example by distillation. The ethylene which has not been transformed may be recycled to the reactor. The catalyst residues included in the heavy fraction may be incinerated.

Products Obtained

The process of the invention can be used for the selective production of but-1-ene. This compound is of use as a co-monomer with ethylene in the manufacture of linear low density polyethylene.

The following examples illustrate the invention.

Example 1

Synthesis of the Complex $[(L7)_2Ti(OiPr)_2]$ 3.6 g (35 mmole) of ligand L7, 10 mL of dry cyclohexane and 5 g (17.5 mmole) of $[Ti(OiPr)_4]$ (where iPr stands for isopropyl) were introduced into a Schlenk flask under argon at ambient temperature. This mixture was then heated under reflux for 30 min and stirred overnight, still under argon. Evaporation of the solvent produced the complex $[(L7)_2Ti(OiPr)_2]$ in the form of an orange oil. The yield was almost quantitative. The structure of the complex was confirmed by $^1H$ and $^{13}C$ NMR analyses.

Example 2

Synthesis of the Complex $[(L8)_2Ti(OiPr)_2]$ 3.4 g (35 mmole) of ligand L8, 10 mL of dry cyclohexane and 5.0 g (17.5 mmole) of $[Ti(OiPr)_4]$ were introduced into a Schlenk flask under argon at ambient temperature. This mixture was then heated under reflux for 30 min and stirred overnight, still under argon. Evaporation of the solvent produced the complex $[(L8)_2Ti(OiPr)_2]$ in the form of a dark orange oil. The yield was almost quantitative. The structure of the complex was confirmed by $^1H$ and $^{13}C$ NMR analyses.

Example 3

Synthesis of the Complex $[(L9)_2Ti(OiPr)_2]$ 3.8 g (35 mmole) of ligand L9, 10 mL of dry cyclohexane and 5.0 g (17.5 mmole) of $[Ti(OiPr)_4]$ were introduced into a Schlenk flask under argon at ambient temperature. This mixture was then heated under reflux for 30 min and stirred overnight, still under argon. Evaporation of the solvent produced the complex $[(L9)_2Ti(OiPr)_2]$ in the form of a colourless oil. The yield was almost quantitative. The structure of the complex was confirmed by $^1H$ and $^{13}C$ NMR analyses.

Example 4

Synthesis of the Complex $[(L11)_2Ti(OiPr)_2]$ 4.3 g (35 mmole) of ligand L11, 10 mL of dry cyclohexane and 5.0 g (17.5 mmole) of $[Ti(OiPr)_4]$ were introduced into a Schlenk flask under argon at ambient temperature. This mixture was then heated under reflux for 30 min and stirred overnight, still under argon. Evaporation of the solvent produced the complex $[(L11)_2Ti(OiPr)_2]$ in the form of an orange oil. The yield was almost quantitative. The structure of the complex was confirmed by $^1H$ and $^{13}C$ NMR analyses.

Example 5

Synthesis of the Complex $[(L12)_2Ti(OiPr)_2]$ 4.0 g (35 mmole) of ligand L12, 10 mL of dry cyclohexane and 5.0 g (17.5 mmole) of $[Ti(OiPr)_4]$ were introduced into a Schlenk flask under argon at ambient temperature. This mixture was then heated under reflux for 30 min and stirred overnight, still under argon. Evaporation of the solvent produced the complex [(L12)$_2$Ti(OiPr)$_2$] in the form of a yellow liquid. The yield was almost quantitative. The structure of the complex was confirmed by $^1$H and $^{13}$C NMR analyses.

Example 6

Synthesis of the Complex [(L14)$_2$Ti(OiPr)$_2$]

3.2 g (14 mmole) of ligand L14, 10 mL of dry cyclohexane and 2.0 g (7 mmole) of [Ti(OiPr)$_4$] were introduced into a Schlenk flask under argon at ambient temperature. This mixture was then heated under reflux for 30 min and stirred overnight, still under argon. Evaporation of the solvent produced the complex [(L14)$_2$Ti(OiPr)$_2$] in the form of a viscous yellow liquid. The yield was almost quantitative. The structure of the complex was confirmed by $^1$H, $^{13}$C and $^{31}$P NMR analyses.

Example 7

Synthesis of the Complex [(L16)$_2$Ti(OiPr)$_2$]

3.4 g (14 mmole) of ligand L16, 10 mL of dry cyclohexane and 2.0 g (7 mmole) of [Ti(OiPr)$_4$] were introduced into a Schlenk flask under argon at ambient temperature. This mixture was then heated under reflux for 30 min and stirred overnight, still under argon. Evaporation of the solvent produced the complex [(L16)$_2$Ti(OiPr)$_2$] in the form of a viscous yellow liquid. The yield was almost quantitative. The structure of the complex was confirmed by $^1$H, $^{13}$C and $^{31}$P NMR analyses.

Example 8

Synthesis of the Complex [(L16)$_2$Ti(OnBu)$_2$]

2.9 g (12 mmole) of ligand L16, 10 mL of dry cyclohexane and 2.0 g (6 mmole) of [Ti(OnBu)$_4$] (where nBu stands for n-butyl) were introduced into a Schlenk flask under argon at ambient temperature. This mixture was then heated under reflux for 30 min and stirred overnight, still under argon. Evaporation of the solvent produced the complex [(L16)$_2$Ti(OnBu)$_2$] in the form of a viscous yellow liquid. The yield was almost quantitative. The structure of the complex was confirmed by $^1$H, $^{13}$C and $^{31}$P NMR analyses and by elemental analysis.

Examples 9 to 16 (in Accordance with the Invention)

Selective Dimerization of CH$_2$H$_4$ 0.15 mmole of the complex [(L)$_n$Ti(OiPr)$_{4-n}$] or [(L)$_n$Ti(OnBu)$_{4-n}$] as described above in the invention, dissolved in cyclohexane, was introduced in order into a stainless steel autoclave with a useful volume of 35 mL, provided with an electric heater and a compressed air vortex cooling system for adjusting the temperature. Next, 0.45 mmole of triethylaluminium in solution in cyclohexane was introduced, i.e. an Al/Ti molar ratio of 3. The total quantity of cyclohexane was 6 mL. Next, ethylene was introduced into the autoclave in order to keep a constant pressure of 2 MPa. After a reaction time "t", ethylene introduction was stopped and the reactor was cooled to ambient temperature. The autoclave was then depressurized and the catalytic system was neutralized by injecting 1 mL of water. A gas fraction and a liquid fraction were recovered, which were analyzed by chromatography. If appropriate, a small quantity of polyethylene was also recovered.

Table 1 below details the results obtained:

TABLE 1

Summary of tests in accordance with the invention

| No | Nature of complex | Time (h) | Productivity (g/gTi/h) | Distribution (wt %) C4 (α1) | C6 (α2) | PE |
|----|-------------------|----------|------------------------|-----------------------------|---------|-----|
| 9  | [(L7)$_2$Ti(OiPr)$_2$]  | 1    | 600  | 95 (99+)   | 3 (15)   | 2    |
| 10 | [(L9)$_2$Ti(OiPr)$_2$]  | 1    | 700  | 91 (99)    | 7.5 (6)  | 0.5  |
| 11 | [(L11)$_2$Ti(OiPr)$_2$] | 1    | 1400 | 94 (99+)   | 5.5 (8)  | 0.5  |
| 12 | [(L8)$_2$Ti(OiPr)$_2$]  | 1    | 800  | 94.5 (99+) | 4.5 (9)  | 1    |
| 13 | [(L12)$_2$Ti(OiPr)$_2$] | 1    | 500  | 95 (99+)   | 4 (11)   | 1    |
| 14 | [(L14)$_2$Ti(OiPr)$_2$] | 0.43 | 3400 | 94 (99+)   | 6 (12)   | <0.5 |
| 15 | [(L16)$_2$Ti(OiPr)$_2$] | 0.22 | 6600 | 92 (99+)   | 8 (12)   | <0.5 |
| 16 | [(L16)$_2$Ti(OnBu)$_2$] | 0.15 | 9700 | 93 (99+)   | 7 (9)    | <0.5 |

In this table, the productivity is defined as the mass of ethylene (CH$_2$H$_4$) consumed per gram of titanium initially introduced, and per hour.

The C4 distribution is the quantity of olefins with a carbon atom number equal to 4 in the total distribution.

(α1) represents the selectivity for but-1-ene in the C4 cut.

Similarly, the C6 distribution is the quantity of olefins with a carbon atom number equal to 6 in the total distribution.

(α2) represents the selectivity for hex-1-ene in the C6 cut.

The selectivity for but-1-ene in the C4 cut and for hex-1-ene in the C6 cut was measured by gas chromatography using a method known to the skilled person.

Examples 17 to 20 (Comparative)

Selective Dimerization of C$_2$H$_4$ by [Ti(OiPr)$_4$] in the Presence of Organic Additives, not in Accordance with the Invention Examples 17 to 20 of Table 2 employed the same conditions as those described in Table 1 (the reaction time was equal to 1 h). These examples illustrate the negative effect of organic additives having heteroatoms but not in accordance with the invention (and thus of interest to the process of the invention) on the productivity of [Ti(OiPr)$_4$] in the selective dimerization of ethylene to but-1-ene.

TABLE 2

Summary of comparative tests

| No | Nature of complex | Nature of external additive | "Additive/Ti" molar ratio | Productivity (g/gTi/h) | Distribution (wt %) C4 (α) | C6 (α) | PE |
|---|---|---|---|---|---|---|---|
| 17 | [Ti(OiPr)$_4$] | THF | 2 | 300 | 97 (99+) | 3 (15) | <0.5 |
| 18 | [Ti(OiPr)$_4$] | Pyridine | 2 | <100 | 99 (99+) | <0.5 | <0.5 |
| 19 | [Ti(OiPr)$_4$] | MeOBu | 2 | 700 | 95 (99+) | <5 | <0.5 |
| 20 | [Ti(OiPr)$_4$] | PPh$_3$ | 2 | 1300 | 96 (99+) | 3.5 (13) | 0.5 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding FR application Ser. No. 10/02.089, filed May 18, 2011, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A catalytic composition comprising:
at least one organometallic titanium complex, and a hydrocarbylaluminium compound as activating agent,
wherein said hydrocarbylaluminium compound is a tris(hydrocarbyl)aluminium compound, a chlorinated or brominated hydrocarbylaluminium compound, or an aluminoxane compound, and
said organometallic complex contains at least one alkoxy ligand functionalized by a heteroatom that is nitrogen, oxygen, phosphorus, sulphur, arsenic or antimony or by an aromatic group and having the formula:

[Ti(OR)$_n$(Y)$_{(4-n)}$]

in which:
Y in each case is a halide, an R'O— alkoxy group, an R'$_2$N— amido group, or a R'COO— carboxylate, where R' is a hydrocarbonyl radical, optionally non-functionalized, containing 1 to 30 carbon atoms;
n is whole values from 1 to 4; and
—OR is an alkoxy ligand the structure of which is below:

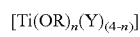
O—(CR$^{10}$R$^{11}$)$_m$—X-L in which:
the functional group L is a group comprising a heteroatom that is arsenic or antimony, or an aromatic group, or L is —NR$^1$R$^2$, —OR$^3$, —PR$^4$R$^5$ or —SR$^6$,
wherein R$^1$ and R$^2$ together are a cyclic hydrocarbon containing 1 to 30 carbon atoms;
wherein R$^3$, R$^4$, R$^5$, R$^6$ each represent a hydrogen atom or a hydrocarbon chain, which is acyclic or cyclic, containing 1 to 30 carbon atoms, the group X represents —CR$^7$R$^8$—, —O— or —NR$^9$—;
the groups R$^7$, R$^8$, and R$^9$ each represent a hydrogen atom or a hydrocarbon chain, which is acyclic or cyclic, containing 1 to 30 carbon atoms, and optionally comprising a heteroatom; and
the group (CR$^{10}$R$^{11}$)$_m$ is —CH$_2$—, —(CH$_2$)$_2$—, —(CH$_2$)$_3$—, —(CH$_2$)$_4$—, —(CH$_2$)$_5$—, —C(CH$_3$)$_2$—, —C(CH$_3$)$_2$—CH$_2$—, —C(CH$_3$)$_2$—CH$_2$—CH$_2$—, —C(CF$_3$)$_2$—, —C(CF$_3$)$_2$—CH$_2$— or —C(CF$_3$)$_2$—CH$_2$—CH$_2$—.

2. A catalytic composition according to claim 1, in which said functional group L is —NR$^1$R$^2$, —OR$^3$, —PR$^4$R$^5$ or —SR$^6$, in which the groups R$^3$, R$^4$, R$^5$, R$^6$ each represent a hydrogen atom or a hydrocarbon chain, which is acyclic or cyclic, containing 1 to 30 carbon atoms.

3. A catalytic composition according to claim 1, in which said functional group L is methoxy, butoxy, pyrrolidino, pyridine, —PR$_2$ in which R is an alkyl or aryl group which is substituted or unsubstituted, thiophene, tetrahydrofuran, furan or phenyl, said groups in each case being substituted or unsubstituted.

4. A catalytic composition according to claim 3, in which said group L is —PR$_2$ in which R is an alkyl or aryl group which is substituted or unsubstituted.

5. A catalytic composition according to claim 1, in which Y is R'O— where R' is a hydrocarbyl radical containing 1 to 30 carbon atoms.

6. A catalytic composition according to claim 1, in which X is CR$^7$R$^8$.

7. The catalytic composition according to claim 1, wherein R' is a non-functionalized hydrocarbonyl radical containing 1 to 30 carbon atoms.

8. The catalytic composition according to claim 1, wherein Y is a chlorine atom.

9. The catalytic composition according to claim 1, in which X is —CH$_2$— or —C(CH$_3$)$_2$—.

10. The catalytic composition according to claim 1, in which —O—(CR$^{10}$R$^{11}$)$_m$—X-L is a ligand of the following formulae L1, L2, and L5-L22:

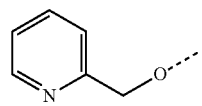

L1

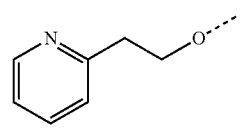

L2

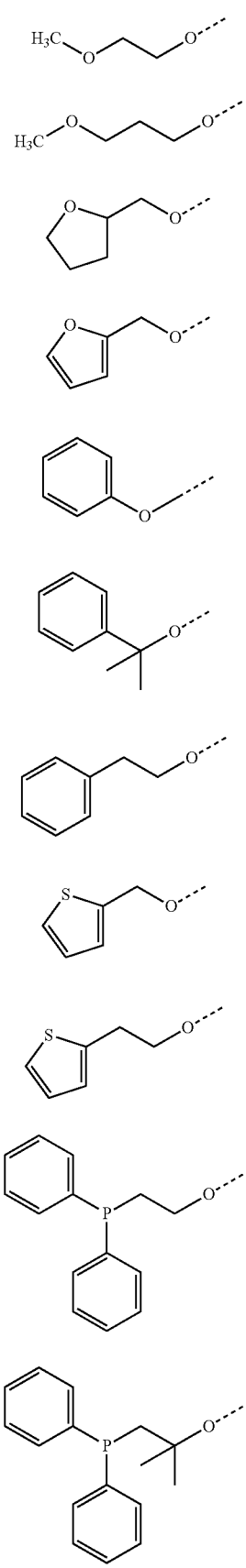
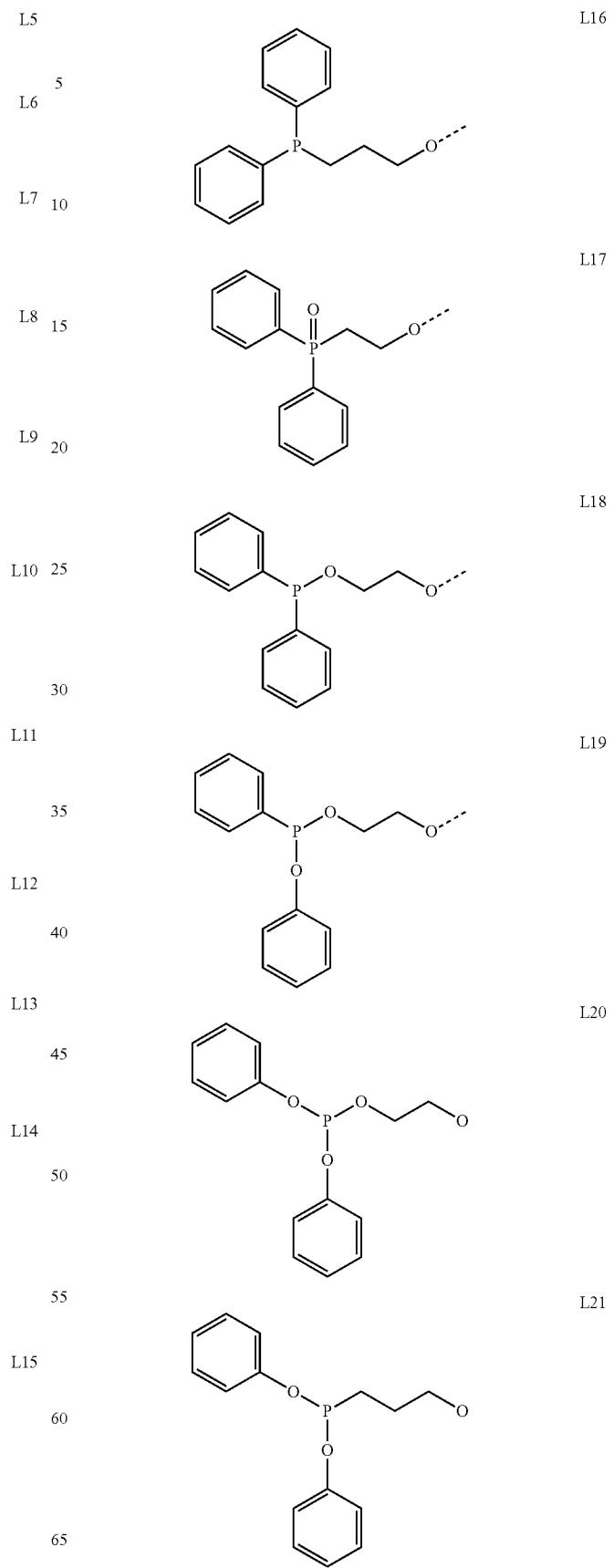

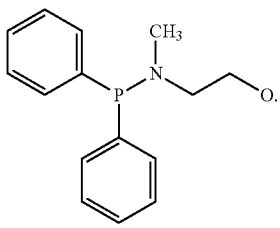

L22

11. The catalytic composition according to claim 10, in which O—$(CR^{10}R^{11})_m$—X-L is a ligand of formulas L7, L8, L9, L11, L12, L14, or L16.

12. The catalytic composition according to claim 11, in which said at least one alkoxy ligand of formula $[Ti(OR)_n(Y)_{(4-n)}]$ is $[(L7)_2Ti(OiPr)_2]$, $[(L9)_2Ti(OiPr)_2]$, $[(L11)_2Ti(OiPr)_2]$, $[(L8)_2Ti(OiPr)_2]$, $[(L12)_2Ti(OiPO_2]$, $[(L14)_2Ti(OiPr)_2]$, $[(L16)_2Ti(OiPr)_2]$, or $[(L16)_2Ti(OnBu)_2]$, wherein L7, L8, L9, L11, L12, L14, and L16 refer to formulas L7, L8, L9, L11, L12, L14, and L16, respectively, iPr stands for isopropyl, and nBu stands for n-butyl.

13. The catalytic composition according to claim 10, in which O—$(CR^{10}R^{11})_m$—X-L is a ligand of formula L7.

14. The catalytic composition according to claim 10, in which O—$(CR^{10}R^{11})_m$—X-L is a ligand of formula L8.

15. The catalytic composition according to claim 10, in which O—$(CR^{10}R^{11})_m$—X-L is a ligand of formula L9.

16. The catalytic composition according to claim 10, in which O—$(CR^{10}R^{11})_m$—X-L is a ligand of formula L11.

17. A process for the selective dimerization of ethylene to but-1-ene employing a catalytic composition according to claim 1.

18. The process according to claim 17, wherein triethylaluminium is used as the activating agent and the molar ratio of activating agent to Ti is in the range 1 to 5.

19. The process according to claim 17, wherein the ethylene dimerization reaction is conducted at a total pressure of 0.5 to 15 and at a temperature of 20° C. to 180° C.

20. The process according to claim 17, wherein the ethylene dimerization reaction is conducted at a total pressure of 1 to 10 MPa and at a temperature of 40° C. to 140° C.

* * * * *

UNITED STATES PATENT AND TRADEMARK OFFICE
CERTIFICATE OF CORRECTION

PATENT NO. : 8,624,042 B2  
APPLICATION NO. : 13/109377  
DATED : January 7, 2014  
INVENTOR(S) : Fabien Grasset et al.

Page 1 of 1

It is certified that error appears in the above-identified patent and that said Letters Patent is hereby corrected as shown below:

In the Claims:

Column 13, line 20: L9 reads

" 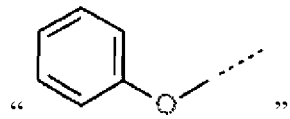 "

should read

-- 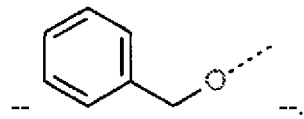 --.

Signed and Sealed this  
Thirteenth Day of May, 2014

Michelle K. Lee  
*Deputy Director of the United States Patent and Trademark Office*